(12) United States Patent  
Clunet-Coste et al.

(10) Patent No.: US 8,597,762 B2  
(45) Date of Patent: Dec. 3, 2013

(54) REINFORCING PREFORM IN THE FORM OF A MESHED GRID AND COMPOSITE MATERIAL WITH PREIMPREGNATED FIBERS FOR A DENTAL PROSTHESIS, AND METHOD FOR PRODUCING THE GRID

(75) Inventors: Bruno Clunet-Coste, Saint Etienne de Crossey (FR); Bernard Maneuf, Voiron (FR); André Collombin, Voiron (FR); Yannick Le Guay, Renage (FR)

(73) Assignees: Bruno Clunet-Coste, Saint Etienne de Crossey (FR); Bernard Maneuf, Voiron (FR); Andre Collombin, Voiron (FR)

( * ) Notice: Subject to any disclaimer, the term of this patent is extended or adjusted under 35 U.S.C. 154(b) by 886 days.

(21) Appl. No.: 12/654,201

(22) Filed: Dec. 14, 2009

(65) Prior Publication Data

US 2010/0151425 A1 Jun. 17, 2010

(30) Foreign Application Priority Data

Dec. 16, 2008 (FR) .................................... 08 07056

(51) Int. Cl.  
*B32B 3/10* (2006.01)

(52) U.S. Cl.  
USPC ............... 428/137; 442/38; 442/43; 442/304; 442/307

(58) Field of Classification Search  
USPC ........................ 442/1–59, 307; 428/131–138  
See application file for complete search history.

(56) References Cited

U.S. PATENT DOCUMENTS

| | | | |
|---|---|---|---|
| 2,755,552 A | 7/1956 | Brandau | |
| 2,793,436 A | 5/1957 | Gotlib | |
| 5,702,991 A * | 12/1997 | Jacobs | ............................ 442/72 |
| 6,010,337 A | 1/2000 | Billet et al. | |
| 6,183,253 B1 * | 2/2001 | Billet et al. | ...................... 433/81 |
| 6,220,862 B1 | 4/2001 | Casellini et al. | |
| 6,244,869 B1 | 6/2001 | Billet et al. | |
| 2007/0025955 A1 * | 2/2007 | Lowinger et al. | .......... 424/78.27 |
| 2007/0041952 A1 * | 2/2007 | Guilak et al. | ................ 424/93.7 |

FOREIGN PATENT DOCUMENTS

| | | |
|---|---|---|
| FR | 2 588 181 A1 | 4/1987 |
| FR | 2 776 502 A1 | 10/1999 |
| JP | A-2007-131654 | 5/2007 |
| WO | WO 98/19621 | 5/1998 |

OTHER PUBLICATIONS

French Search Report for French Patent Application No. 0807056, issued Jun. 29, 2009.

* cited by examiner

*Primary Examiner* — Elizabeth Cole  
(74) *Attorney, Agent, or Firm* — Oliff & Berridge, PLC

(57) ABSTRACT

A preform made of composite material designed to be formed on a laboratory model and to be integrated in a base plate of a dental prosthesis.

The preform comprises a grid formed by a meshing of weft threads and warp threads coated in an impregnating resin, the space between the meshes being exempt of fibers and resin, and determining a surface of free spaces of more than 25% of the total surface of the grid. The weft threads are fixed onto the warp threads at the nodes of the meshing to enable the preform to be handled and to be formed on a laboratory model, without the impregnating resin creeping into the spaces of the meshes.

5 Claims, 4 Drawing Sheets

REINFORCING PREFORM IN THE FORM OF A MESHED GRID AND COMPOSITE MATERIAL WITH PREIMPREGNATED FIBERS FOR A DENTAL PROSTHESIS, AND METHOD FOR PRODUCING THE GRID

BACKGROUND OF THE INVENTION

The invention relates to a photopolymerizable preimpregnated reinforcing element formed by a composite material with a fiber and particle base, and designed to reinforce base plates of removable dental prostheses.

STATE OF THE ART

The document U.S. Pat. No. 2,755,552 describes strengtheners formed by fibers to reinforce dental prostheses, crowns or splints.

The document U.S. Pat. No. 2,793,436 refers to a system for reinforcing fixed or removable dental prostheses with crossed or parallel fibers or any other weaving texture, able to be colorless, transparent or opalescent.

The document FR 2 588 181 discloses the use of composite material fibers to reinforce dental prostheses made from a totally or partially polymerized resin base, manufactured by pultrusion, injection, compression, molding, or transfer.

Known reinforcing prostheses are generally constituted by metal grids or metal base plates. The injected resin penetrates into the meshes of the metal grid. The drawback of metal grids remains the electrocorrosion effect that can occur with time.

Manufacturing base plates of removable prostheses made from dental resin obtained by injection, pressing or suction in the laboratory, is also known. The problem to be overcome is to integrate the reinforcement correctly in the resin to constitute a single composite laminate. In known preimpregnated strengtheners, the reinforcing fibers are totally incorporated in the resin. Once polymerized on a model, they form a solid structure. They are incorporated sandwiched in the resin of the prosthesis, but the resin cannot penetrate into the structure which does not have any free spaces. The document U.S. Pat. No. 6,010,337 discloses a support shell made from composite material reinforced with fibers, said shell being constituted by forming of a photopolymerizable preform on a model. The support shell is rigid and its solid surface does not enable resin to be injected.

OBJECT OF THE INVENTION

A first object of the invention consists in providing a preform in the form of a grid for dental use that is preimpregnated and presents a surface of free spaces between the meshes of at least 25% of the surface of the fabric exempt of fibers or impregnating resin. The weft threads cross the warp threads at regular intervals and cannot slide on the warp threads. The warp and weft threads are themselves formed by woven fibers. The threads are selectively coated with resin which may be doped with particles in the state prior to polymerization and the central space of each mesh thus formed is exempt of resin.

A second object of the invention is to develop a method for forming such a preimpregnated preform on a laboratory model so as to constitute a solid grid formed by meshing of warp threads and weft threads after polymerization, the central space of the grid being exempt of fibers and resin.

The forming means used in the state of the art use forming machines under pressure or in a vacuum. In the document U.S. Pat. No. 6,010,337, a transparent membrane presses the preimpregnated preform onto a model, and the pre-impregnated preform is then polymerized in visible light. This technique has the drawback of crushing the preimpregnated preform, and the final composite becomes compact, without porosity, and rigid. This method prohibits the arrangement of spaces without fibers and without resin enabling a resin to be injected extemporaneously.

The forming method according to the invention is characterized by the following steps consisting in:
 placing a preform on a laboratory model insulated beforehand by a first insulating foil, said preform being formed by a meshing of weft threads and warp threads coated in an impregnating resin to form a grid in the state prior to polymerization,
 placing a micronic second insulating foil on the grid,
  covering micronic second insulating foil by means of a thermoplastic membrane that is heated and softened to be applied by pressure or negative pressure on the grid, the thermoplastic material of the membrane having crept into the spaces between the meshes,
 cooling membrane to constitute a rigid support shell of grid (1),
 photopolymerizing grid in the support shell,
  and detaching grid from the shell to be integrated in a base plate of a prosthesis.

Such a forming method preserves the initial configuration of the pre-impregnated preform after forming.

The method was formulated to preserve the intermesh spaces between the warp threads and weft threads, exempt of fibers and impregnating resin. The method prevents the impregnating resin from creeping into the mesh spaces when forming takes place on the dental laboratory model so as to constitute a genuine grid after polymerization.

It was established that, after softening by heat and placing on a grid in the state prior to polymerization according to the invention, a thermoplastic membrane was able to invest the mesh spaces free of fibers and resin. The thermoplastic membrane can be a membrane made from vinyl ethyl acetate or from any other thermoplastic product.

After it has been softened and placed on the previously insulated model, the material of the membrane invests the free spaces of the grid and prevents the impregnating resin from creeping into the free spaces of the grid. After cooling, it constitutes a shell molded on the laboratory model the grid whereof is provisionally maintained by the retention procured by the thermoplastic membrane investing the free spaces between the grid meshes.

The assembly is then transferred to a laboratory photopolymerization chamber and the grid according to the invention is hardened in its forming shell. The shell is then removed, providing a grid of composite material reinforced with the completely polymerized fibers and particles, with a large proportion of free spaces at least equal to 25% of the total surface of the grid, the spaces exempt of fibers and resin being at least equal to the width of the weft and warp threads proper.

A third object of the invention is to enable injection, pressing or suction of a dental resin, for example PMMA, constituting a basis for an acrylic mobile prosthesis, in the spaces exempt of fibers and impregnating resin formed between the warp threads and weft threads, so as to constitute a fiber-reinforced laminate. The dental resin is integrated in the grid, forming a composite laminate at the end of the method.

The resin impregnating the warp threads and weft threads is advantageously of the same chemical nature as the resin constituting the prosthesis base, it is chemically linked.

BRIEF DESCRIPTION OF THE DRAWINGS

Other advantages and features will become more clearly apparent from the following description of a particular embodiment of the invention given for non-restrictive example purposes only and represented in the appended drawings, in which.

DESCRIPTION OF A PREFERRED EMBODIMENT OF THE INVENTION

Figure 1:
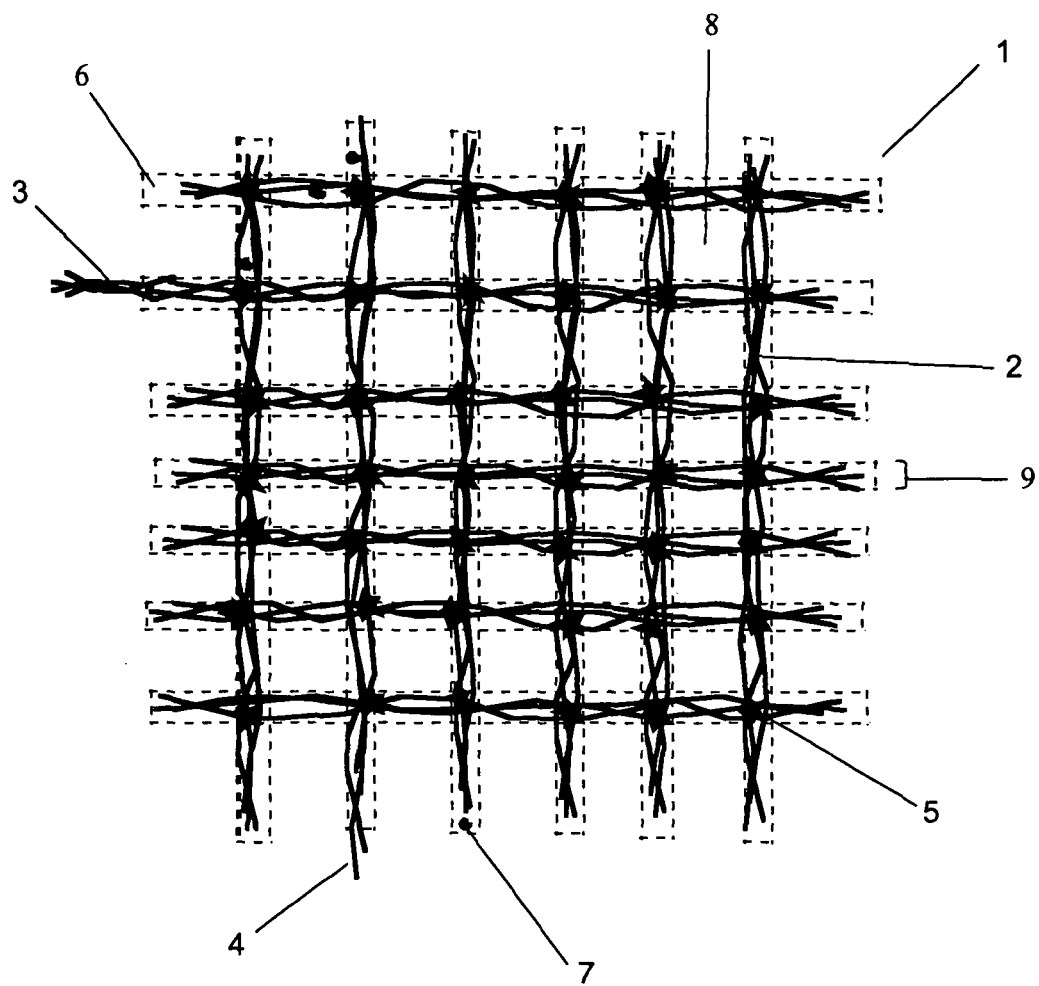
FIG. 1 is a schematic plane view of a grid according to the invention.

With reference to FIG. 1, a preform is constituted by a meshing of weft threads 2 and warp threads 3, both of which are formed by woven fibers 4 to form a grid 1. Weft threads 2 are fixed to warp threads 3 at the nodes 5 of the meshing so as to limit sliding thereof which is always less than their own cross-section.

Each fiber 4 is impregnated with an impregnating resin 6 that may be doped with particles 7 or not to give it a gel state prior to polymerization. The space 8 between the meshes of the meshing is exempt of fibers and resin so as to constitute grid 1. Space 8 is larger than cross-section 9 of weft threads 2 and warp threads 3. Resin 6 can be a methacrylate resin able to bind chemically with glass fibers after prior silaning treatment.

Figure 2:
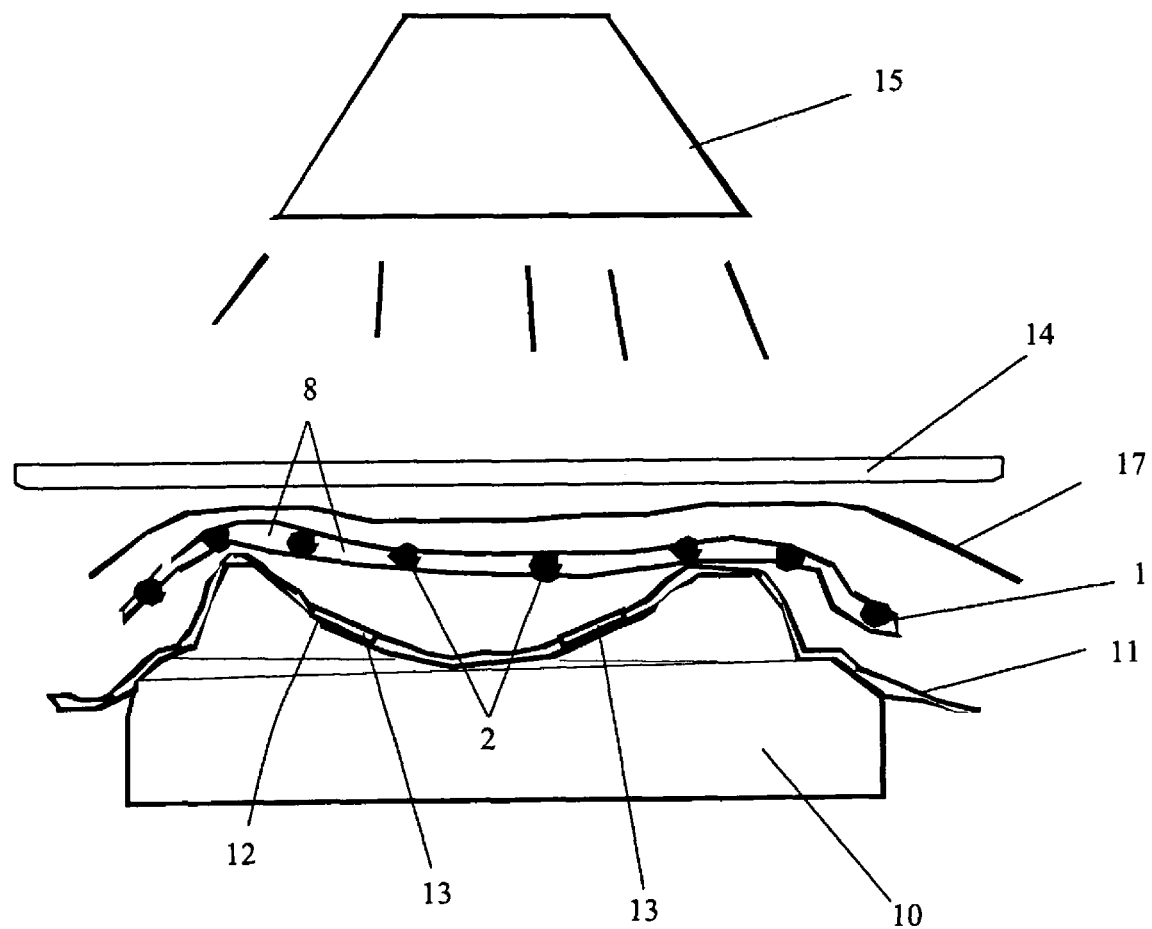
FIG. 2 is a schematic view of a grid according to the invention positioned prior to polymerization on a laboratory model.

In FIG. 2, a plaster laboratory model 10 is insulated with a first insulating foil, 11 which is perforated in several places to form diaphragms 12 which are filled with resin to act as depression wedges 13. Insulating foil 11 can be a sheet of cellophane, and the preform in the form of grid 1 of FIG. 1 is positioned on foil 11.

A second insulating foil 17 of micronic thickness then covers grid 1. A membrane 14 made from thermoplastic material, in particular vinyl ethyl acetate, is superposed on the preparation, which can finally be exposed with heating and placing means 15.

Figure 3:
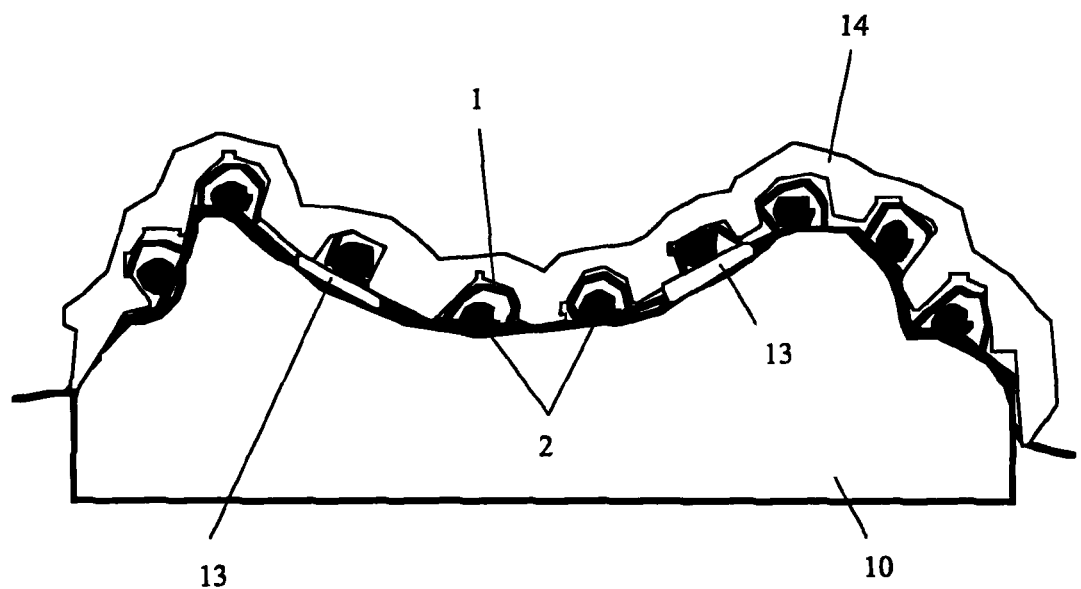
FIG. 3 is a schematic view of a grid according to the invention polymerized in its support shell.

With reference to FIG. 3, the previously heated thermoplastic membrane 14 is applied on the preparation after softening, and grid 1 is formed on insulated model 10. The intermesh spaces 8, exempt of resin and fibers, are invested by the thermoplastic material of membrane 14, preventing resin 6 from creeping. Membrane 14 thereby acts as forming shell to apply grid 1 on a model. Depression wedges 13 arrange a space between grid 1 and model 10 after first insulating foil 11 has been removed. Wedges 13 are thereby securely attached to grid 1.

Figure 4:
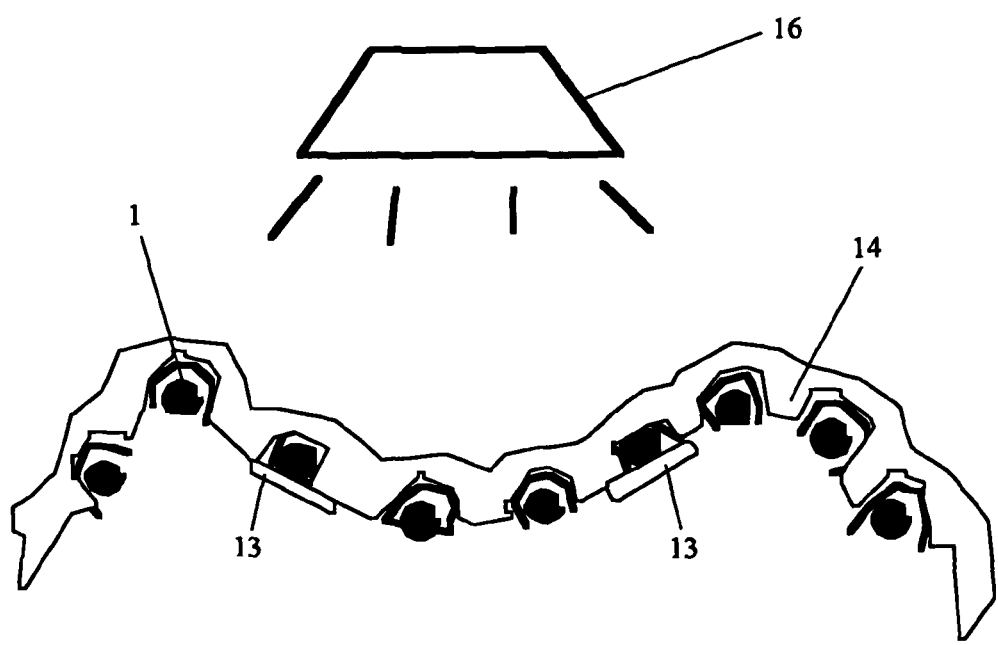
FIG. 4 is a schematic view of a grid according to the invention in its thermoplastic forming shell after cooling, with the spaces between the meshes exempt of fibers and resin invested by the thermoplastic material, and transferred to a laboratory chamber for photopolymerizing resins.

With reference to FIG. 4, grid 1 remains housed in its thermoplastic shell hardened by cooling, and is then transferred to a visible-light polymerization chamber 16.

Figure 5:
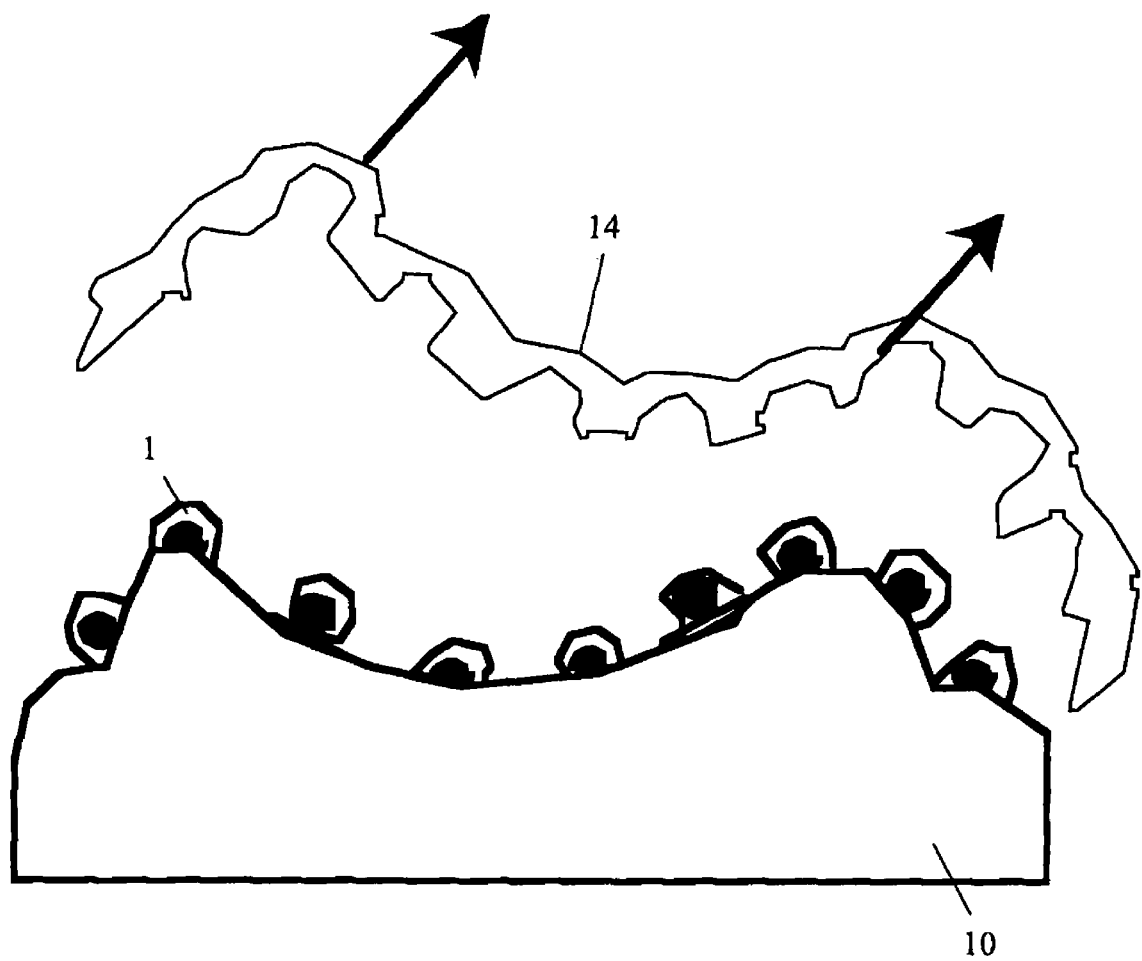
FIG. 5 is a schematic view of a laboratory model on which the polymerized grid is repositioned with the separate thermoplastic membrane, leaving the spaces between the meshes exempt of fibers and resin.

With reference to FIG. 5, thermoplastic membrane 14 of the forming shell is removed and grid 1 is positioned on laboratory model 10.

The invention claimed is:

1. A preform for a base plate of a dental prosthesis, designed to be formed on a laboratory model, comprising:
   weft threads and warp threads formed by fibers with an impregnating resin, wherein the warp threads are configured to form a grid by meshing with the weft threads, said grid having apertures representing a surface of more than 25% of the total surface of the grid; and
   a membrane pressed onto the grid for filling said apertures, and preventing creeping of the impregnated resin, wherein the membrane is made of a thermoplastic material and configured to be removable from the grid,
   wherein the preform comprises apertures representing a surface of more than 25% of the total surface of the grid after the membrane is pressed onto the grid.

2. The preform according to claim 1, wherein the weft threads are maintained by knitting at equal distance from one another on the warp threads and sliding thereof on the warp after forming on a laboratory model is less than their cross-section.

3. The preform according to claim 1, wherein the warp threads are maintained by knitting at equal distance from one another on the weft threads and sliding thereof on the weft after forming on a laboratory model is less than their cross-section.

4. The preform according to claim 1, wherein the weft threads and warp threads are coated by a resin gel in the state prior to polymerization of the preform, and the apertures between the meshes are exempt of fibers and resin.

5. The preform according to claim 1, wherein each free aperture is greater than or equal to the width of the weft and warp threads after forming on a laboratory model.

* * * * *